United States Patent [19]
Baylink

[11] Patent Number: 5,807,822
[45] Date of Patent: Sep. 15, 1998

[54] INSULIN-LIKE GROWTH FACTOR II AS A PHARMACEUTICAL AGENT IN THE TREATMENT OF OSTEOPENIAS

[75] Inventor: David J. Baylink, Redlands, Calif.

[73] Assignee: British Biotechnology Ltd.

[21] Appl. No.: 993,953

[22] Filed: Dec. 18, 1992

Related U.S. Application Data

[63] Continuation of Ser. No. 556,879, Jul. 20, 1990, abandoned, which is a continuation of Ser. No. 43,628, Apr. 28, 1987, abandoned, which is a continuation-in-part of Ser. No. 676,202, Nov. 27, 1984, abandoned, which is a continuation of Ser. No. 501,329, Jun. 6, 1983, abandoned.

[51] Int. Cl.$^6$ .......................... A61K 38/30; A61K 35/55
[52] U.S. Cl. .................................. 514/12; 514/2; 514/8; 514/21; 424/562
[58] Field of Search ............................ 514/2, 8, 21, 860, 514/12; 424/562

[56] References Cited

PUBLICATIONS

Perdue, *13th Int. Cancer Congress* Part B Biol. of Cancer pp. 405–413 1983 "The Role of Somatomedin/Insulin Like Growth Factors and Their Receptors in Skeletal Growth and Fetal Development: a Mini Review".

Rinderknecht et al *Proc Natl Acad Sci* vol. 73 pp. 2365–2369 1976 "Polypeptide with Nonsuppressible Insulin–Like and Cell Growth Promoting Activities in Human Serum: Isoaltion, Chemical . . . ".

Rinderknecht et al *FEBS Lett* vol. 89(2) May 1978 "Primary Structure of Human Insulin–Like Growth Factor II".

Bennett et al *Endocrinology* vol. 115 pp. 1577–1583 1984 "Characteriztion of Insulin–Like Growth Factor I Receptors on Cultured Rat Bone Cells: . . . ".

Canalis *J Clin Invest* vol. 66 Oct. 1980 pp. 709–719 "Effect of Insulin Like Growth Factor I on DNA and Protein Synthesis in Cultured Rat Calvaria".

Baylink et al *Clin Orthoped* vol. 55 pp. 51–85 1967.

Schoenle et al. (1982) 64$^{th}$ Annual Necking Endocrine Society, Abstr. 325.

Frost et al. Bone & Mineral 18(1982) 227–236.

Postel–Vinay et al. Exper. Cell. Res. 148(1983) 105–116.

Bennett et al. J. Clin. Endocrinol. Metab. 59(1984) 701–704, Cited and Provided as BIOSIS Abstract No.: 75030087.

Schmid et al. Calcif. Tissue Int. 35(1983) 578–585, Cited as and Provided as BIOSIS Abstract No.: 77018221.

Potan et al. Biochem Biophys. Res. Comm. 119(1984) 359–364 (Feb.).

The Merck Manual of Diagnosis & Therapy Merck Research Labs, New Jersey, 1992, pp. 1357–1359.

*Primary Examiner*—John L. LeGuyader
*Attorney, Agent, or Firm*—Felfe & Lynch

[57] ABSTRACT

The present invention relates to an improved method of treating osteopenias, particularly osteoporosis, in mammals comprising administering a therapeutically effective amount of a pharmaceutical formulation agent comprising the polypeptide Insulin-like Growth Factor II or an osteoblastic stimulating fragment thereof, either alone or in the presence of a potentiating amount of fluoride ion, and in a pharmaceutically acceptable carrier.

The invention further relates to a method of preventing osteopenias in a susceptible population of mammals consisting of administering a prophylactically effective amount of the pharmaceutical agent described above.

1 Claim, No Drawings

INSULIN-LIKE GROWTH FACTOR II AS A PHARMACEUTICAL AGENT IN THE TREATMENT OF OSTEOPENIAS

This application is a continuation of application Ser. No. 07/556,879 filed Jul. 20, 1990, now abandoned, which is a continuation of Ser. No. 07/043,628 filed Apr. 28, 1987, now abandoned which was a CIP of Ser. No. 06/676,202 filed Nov. 27, 1984, now abandoned which was a continuation of Ser. No. 06/501,329 filed Jun. 6, 1983, now abandoned.

BACKGROUND OF THE INVENTION

A. Field of the Invention

Bone wasting diseases (osteopenias). Osteopenia is a general term used to describe any bone wasting disease, regardless of cause (i.e., whether it arises from a net predominance of bone resorption or a net deficit of bone formation) which results in a deficit of bone mass. Osteoporosis is one of the bone wasting diseases, characterized by a net loss of bone mass due to bone resorption exceeding bone formation, which leads to an atraumatic fracture. There is a rarefaction of bone to leave the skeleton weakened and unable to bear the normal stresses imposed on it. The disease is therefore particularly prevalent in the parts of the skeleton that are weight bearing, especially the spine and hips. The etiology of the disease is multifactorial, but one common form of the disease occurs after the menopause. Post-menopausal osteoporosis affects 15 million women in the United States alone, and therefore poses a significant health problem.

It is of great importance to be able to provide a drug, or combination of drugs, that may restore bone mass and therefore can be used to treat the osteopenias, particularly osteoporosis.

The present invention is useful because it relates to a pharmaceutical agent, Insulin-like Growth Factor-II (IGF-II) and a combination of pharmaceutical agents, IGF-II and fluoride, which can be used to treat or prevent the osteopenias, particularly osteoporosis.

B. Description of the Prior Art

Sodium fluoride stimulates bone formation in vivo (see Baylink and Bernstein, *Clin. Orthop,.* 55, 51–85, 1967; Haas, et al., *Eur. J. Clin. Invest.,* 3, 235, 1973; Lane et al., *Ortho. Clin. N. Amer.,* 15, 729–745 1984) by a direct mitogenic effect on bone cells. (See Farley et al., *Science,* 222, 330–332, 1983). Bone mineral density of the axial skeleton of patients treated with fluoride increases, and the serum alkaline phosphatase level, an index of bone formation in the skeleton, increases with fluoride treatment. See Ivey, *Clin. Res.* 29: 95A, (1981).

When osteoporotic patients are provided with fluoride therapy, they have demonstrated improved calcium balance, increased trabecular bone volume, decreased fracture frequency and markedly stimulated bone formation. See, D. J. Baylink & D. J. Bernstein, *Clin. Orthop.,* 55, 51–85 (1967); J. R. Cameron, et al., *Clin. Orthop.,* 114, 352–357 (1976).

However, the increase in bone density is slow. For example, the increase in spinal bone density becomes significant after 12 to 18 months of fluoride therapy.

Moreover, fluoride treatment is not equally effective in all patients. Some patients respond poorly to fluoride. Others do not respond at all. See Riggs et al., *J. Amer. Medical Assoc.,* 243, 446–449 (1980).

Thus, there exists a need not only to increase the rate of stimulation of bone formation by fluoride but also to elicit a bone formative response in all treated patients.

It has been suggested that the regulation of bone mass and the growth of bone cells is controlled by a factor localized in the bone. Farley et al., *Program and Abstracts of 61st Annual Meeting of the Endocrine Society* (1979); Howard and Baylink, *Clinical Research,* 28, 50A (1980).

Farley and Baylink, *Biochemistry,* 21, 3502–07 (1982), and Farley et a.l, *Biochemistry,* 21 3508–13 (1982) describe the isolation and partial characterization of skeletal growth factor (SGF) from human bone. According to a pending publication, Mohan, Baylink, et al., have characterized the skeletal growth factor (SGF) as being homogolous and antigenically identical with the known peptide, Insulin-like Growth Factor II (IGF-II).

IGF-II has an amino acid sequence of 67 amino acid residues cross-linked by three disulfide bridges (Formula I), and has a calculated molecular weight of 7471. Rinderknecht, et al., *J. Biol. Chem.,* 253, 2769–76 (1978); *F.E.B.S. Letters,* 89, 283–86 (1978). Brown et al., *J. Receptor Res.,* 5, 297 (1985), have shown that physiological concentrations of IGF-II stimulates thymidine incorporation by primary cultures of activated human T lymphocytes. IGF-II has been shown to enhance erythroid colony formation by human bone marrow cells, Dainniak and Kreczuko, *J. Clin. Inves.,* 76, 1237 (1985); and may be involved in the beta transforming growth factor induced transformation of normal rat kidney (NRK) cells in soft agar. Massague et al., *J. Biol. Chem.,* 260, 455 (1985).

Clinical observations have led to the hypothesis that somatomedins (like IGF-II) are the product of growth hormone action and have a negative feedback on growth hormone secretion. However, Wilson discloses that serum levels of IGF-II, determined by radioimmuno or radioreceptor assays, were not significantly different in growth hormone toxic (acromegalics) or growth hormone deficient subjects but are significantly elevated in the third trimester of pregnancy to return to lower levels after delivery. (Wilson et al., *J. Clin. Endo. Meta.,* 55, 858, 1982).

There is a decline in serum IGF-II levels with age in normal women (644±1135 ng/ml in the eighth decade versus 723±217 ng/ml in the third decade, n=57).

Several small factors (polypeptides) which affect skeletogenesis (bone formation) were reported in *Current Advances in Skeletogenesis,* Eds. Silberman and Slavkin, Amsterdam, Exerpta medica (1982).

Formula I: Amino-acid sequence of IGF-II.

Ala—Tyr—Arg—Pro—Ser—Glu—Thr—Leu—Gly—Gly—Gly—Glu—Leu—Val—Asp—Thr—Leu—Gln—Phe—Val    I
                                         10                                              20

Cys—Gly—Asp—Arg—Gly—Phe—Tyr—Phe—Ser—Arg—Pro—Ala—Ser—Arg—Val—Ser—Arg—Arg—Ser—Arg
                                         30                                              40

Gly—Ile—Val—Glu—Glu—Cys—Cys—Phe—Arg—Ser—Cys—Asp—Leu—Ala—Leu—Leu—Glu—Thr—Tyr—Cys—
                                         50                                              60

—Ala—Thr—Pro—Ala—Lys—Ser—Glu

SUMMARY OF THE INVENTION

It has been discovered that the active peptide, skeletal growth factor (SGF) referred to in Ser. No. 501,325 now abandoned and in the CIP Ser. No. 676,202 now abandoned is in fact the known peptide, Insulin-like Growth Factor II (IGF-II).

The present invention encompasses a pharmaceutical agent for treating and preventing the osteopenias in mammals, particularly osteoporosis, said pharmaceutical agent comprising a therapeutically effective amount of the polypeptide Insulin-like Growth Factor II or an osteoblastic stimulating fragment thereof, in a pharmaceutically acceptable carrier.

In a particularly preferred embodiment of the present invention, the pharmaceutical agent for treating said disease states comprises a therapeutically effective amount of the polypeptide Insulin-like Growth Factor II or an osteoblastic stimulating fragment thereof, in combination with a potentiating amount of fluoride ion in a physiologically acceptable form, in conjunction with a pharmacologically acceptable carrier.

The present invention also encompasses an improved method of treating an osteopenia in mammals, particularly osteoporosis, comprising administering a therapeutically effective amount of Insulin-like Growth Factor II, or an oteoblastic stimulating fragment thereof, either alone or in combination with a potentiating amount of fluoride ion, in a pharmaceutically acceptable carrier to a patient in need of such treatment.

The present invention further encompasses a method of preventing an osteopenia in mammals, particularly osteoporosis, comprising administering a prophylactically effective amount of Insulin-like Growth Factor II, or an osteoblastic stimulating fragment thereof, either alone or in combination with a potentiating amount of fluoride ion, in a pharmaceutically acceptable carrier to a patient susceptible to said disease state.

BRIEF DESCRIPTION

The present invention relates to a new use for an old compound, Insulin-like Growth Factor II.

In particular, the present invention relates to an improved method for treating the osteopenias in mammals, particularly osteoporosis, which provides more effective treatment for all patients suffering from an osteopenia than fluoride therapy alone.

The present invention also relates to the use of a pharmaceutical agent in the method of treating an osteopenia, wherein the pharmaceutical agent is comprised of the 67 amino acid polypeptide, Insulin-like Growth Factor II (calculated MW approximately 7471 Daltons), or a fragment of Insulin-like Growth Factor II, which also possesses osteoblastic stimulating activity, in a pharmaceutically acceptable carrier. Said pharmaceutical agent, IGF-II, is structurally homologous with skeletal growth factor (SGF).

The present invention further relates to the discovery that fluoride ion unexpectedly potentiates the action of IGF-II on the proliferation of bone cells. Accordingly, IGF-II in combination with fluoride ion is particularly preferred as a pharmaceutical agent in the treatment of the osteopenias, particularly osteoporosis. The fluoride ion targets the IGF-II particularly to bone.

Because the susceptibility to osteoporosis in a well-defined population, post menopausal women, is particularly high, and because of the osteoblastic enhancing activity of the pharmaceutical agents of the present invention, these agents may be utilized prophylactically to enhance or maintain osteoblastic (bone building) activity in the patient, thereby preventing the onset of the predominant osteoblastic (bone resorbing) activity observed in the disease state. However, forms of osteoporosis exist other than post-menopausal, including primary and many forms of secondary osteoporosis. These agents may also be used therapeutically or prophylactically in the treatment of all forms of osteoporosis, whether primary or secondary, and in all bone wasting diseases.

DETAILED DESCRIPTION

The present invention relates to methods of treating and preventing the bone wasting disorders known as osteopenias, particularly osteoporosis (whether idiopathic or secondary).

By osteopenia is meant disorders of bone such as osteogenesis imperfecta, osteomalacia, osteitis deformans, osteoporosis, rickets, fibrous dysplasia and the like. By osteoporosis is meant idiopathic wasting disorders of bone such as osteoporosis of aging, or osteogenesis imperfecta, and secondary osteoporosis (eg. resulting secondarily to other disease states such as eunuchoidism, hyperthyroidism, Cushing's syndrome, hyperparathyroidism, hypopituitarism, gluten enteropathy, post-gastrectomy syndrome, glomerulo-osteodystrophy, tubular disorders, vitamin D intoxication, immobilization, respiratory acidosis or inadequate dietary intake of vitamin C, calcium, phosphorus or protein, etc. etc.). However, it is also envisioned that Insulin-like growth factor-II (IGF-II) could be useful in the treatment of impaired bone growth or in the enhancement of traumatic or surgical fracture repair, wherein surgical fractures include bone implants, or augmentation of bony incorporation of prostheses. In particular, the present invention relates to a pharmaceutical agent comprising the peptide, IGF-II or an osteoblast stimulating fragment thereof, either alone or in the presence of a potentiating amount of fluoride ion in a pharmaceutically acceptable carrier. It has been discovered that the active peptide, skeletal growth factor, referred to in Ser. No. 501,325 and in the CIP Ser. No. 676,202 is the known peptide, Insulin-like Growth Factor-II. IGF-II belongs to the family of growth factors that also comprise Insulin, Relaxin, Insulin-like Growth Factor-I (IGF-I) and possibly the beta subunit of the 7s nerve growth factor. See Blundell and Humbell, *Nature,* 287, 781, (1980). IGF-II differs from the other members of its family by molecular weight, amino-acid sequence and the length of its connecting peptide.

In the present invention, IGF-II has been found to stimulate osteoblastic (bone building) activity both when administered in vivo as a semi-purified extract and when added in purified form to bone cell cultures (in vitro).

Two separate in vivo experiments were conducted on rats. In both experiments the rats in the Treated group were parenterally administered a bovine bone IGF-II extract. The rats in the Control group were administered a placebo. The data from Experiment 1 are presented in Tables 1 and 2. Experiment 1 consisted of 5 rats in the Control group and 3 rats in the Treated group.

In Table 1, the parameters measured in the Treated and Control groups consisted of the following (1) serum calcium; (2) body weight at the start of the experiment; (3) body weight at the end of the experiment; (4) femur alkaline phosphatase activity; and (5) femur acid phosphatase activity. As to the first three parameters, no significant (N.S.)

difference was demonstrated between the Control group, which was not receiving IGF-II, and the Treated group, which was receiving bovine bone IGF-II extract.

However, as to parameter 4, the femur alkalinephosdhatase, there was a significant difference between the Treated and Control groups. Specifically, in the Treated Group, the femur alkaline phosphatase was increased 136% over that in the Control group. Increased alkaline phosphatase activity in bone by itself is suggestive of increased osteoblastic (bone building) activity. However, when combined with the data in Table 2, showing the results of histomorphometric assessment of the rat bones, the result is indicative of increased osteoblastic activity within the bone.

TABLE 1

In Vivo Effect Of Bovine Bone IGF-II Extract On Rats (Experiment 1)

| | Parameter | Control | Treated[a] | p[b] |
|---|---|---|---|---|
| 1. | Serum Calcium (mg %) | 9.8 (±0.7) | 9.0 (±0.5) | NC[c] |
| 2. | Body Weight (Start) | 104 (±3.7) | 105 (±4.2) | NS |
| 3. | Body Weight (End) | 147 (±0.9) | 147 (±9.2) | NS |
| 4. | Femur Alkaline Phosphatase (mU/mg protein) | 4.9 (±0.9) | 11.6 (±1.2) | <0.001 |
| 5. | Femur Acid Phosphatase Tartrate Insensitive (mU/mg protein) | 3.4 (±0.4) | 4.8 (±0.3) | <0.02 |

[a]All data reported as mean ± S.E.M. and based on observations from 5 rat s in the control group and 3 rats in the treated group.
[b]Comparisons of treated versus control were by the students' T test.
[c]Not significant at the $p < 0.05$ student T test.

TABLE 2

Histological Assessment of In Vivo Effect Of Bovine Bone IGF-II Extract On Rats (Experiment 1)

| Parameter | Control | Treated[a] | p[b] |
|---|---|---|---|
| 1. Tibiae Periosteal Bone Formation (mm$^3$) | 0.23 (±0.02) | 0.40 (±0.02) | <0.001 |
| 2. Tibiae Periosteal Bone | 6.75 (±0.43) | 8.60 (±0.46) | <0.05 |
| 3. Tibiae Medullary Cavity (mm$^3$) | 0.67 (±0.03) | 0.81 (±0.09) | <0.05 |
| 4. Vertebral Forming Surface (single + double label) % total surface | 58.3 (±2.5) | 90.5 (±1.7) | <0.001 |
| 5. Vertebral Neutral Surface (no label) % (total surface - V.F.S.) | 41.7 (±1.9) | 9.5 (±1.4) | <0.001 |

[a]All data reported as mean ± SEM and based on observation from 5 rats in the control group and 3 rats in the treated group.
[b]Comparisons of treated versus control were by the students' T test.
[c]Not significant at the $p < 0.05$ student T test.

The most dramatic effect of IGF-II extracts on bone is seen in the data in Table 2. Table 2 reflects histological comparisons between the tibiae and vertebrae (bones) of the Treated and Control groups of rats from Experiment 1 after sacrifice. The (IGF-II extract) Treated group demonstrates markedly increased bone growth over the Control group in parameters associated with bone growth. Specifically, relative to the Control group, the Treated group demonstrated 73.9% more tibiae periosteal bone formation (the volume of new bone formed in the outer connective tissue, periosteum, covering the bone); and a 27.4% greater periosteal apposition rate (the rate of laying down of new bone)—parameters 1 and 2 of Table 2.

Moreover, the IGF-II extract Treated group also exhibited a 55% increase in bone forming surface over the untreated Control group, as measured by the ability of the bone forming surface to pick up a label—parameter 4 of Table 2. Alternatively, when this same data is viewed from the perspective of inactive bone forming surface, the data discloses that the Control group had 339% more inactive bone forming surface than the Treated group—parameter 5 of Table 2.

Thus Experiment 1 demonstrates that parenteral administration of IGF-II extract stimulates significant osteoblastic activity in vivo.

The data in Tables 1 and 2, also suggest that additional activity within the bone may also be stimulated. The increase in tartrate insensitive acid phosphatase activity that was observed in the Treated group is due to increased either osteoclastic (bone resorbing) activity or to increased osteoblastic activity. The increased osteoclastic activity was not verified by histological staining. On the other hand, the increase in the tibial medullary cavities area by 21%, parameter 3 of Table 2, is suggestive of some increased osteoclastic (bone resorbing) activity.

This increase in osteoclastic activity, however, is due to the presence of small amounts of transforming growth factor (TGF) in the bovine bone extract. Later studies employing pure IGF-II to treat bone cells in culture demonstrate no such osteoclastic effect. Moreover, TGF is recognized as a potent stimulator of osteoclastic (bone resorbing) activity.

TABLE 3

In Vivo Effect Of Bovine Bone IGF-II Extract On Rats (Experiment 2)

| | Parameter | Control | Treated[a] | p[b] |
|---|---|---|---|---|
| 1. | Serum Calcium (mg %) | 10.7 (±0.3) | 11.1 (±0.3) | NS[c] |
| 2. | Serum Phosphate (mg/dl) | 4.7 (±0.5) | 5.8 (±0.2) | <0.05 |
| 3. | Serum Alkaline Phosphatase (mU/mg protein) | 63.7 (±2.2) | 91.7 (±5.2) | <0.001 |
| 4. | Body Weight (Start) | 86.4 (±0.2) | 85.0 (±0.6) | NS |
| 5. | Body Weight (End) | 149.8 (±2.6) | 147.7 (±2.5) | Ns |

[a]All data reported as mean ± S.E.M. and based on observations from at least 10 rats in each group.
[b]Comparisons of treated versus control were by the students' T test.
[c]Not significant at $p < 0.05$.

TABLE 4

Effect of Bovine Bone IGF-II Extract on Enzyme Activity Within The Bones of Rats. (Experiment 2)

| | Alkaline phosphatase[a] (mU/gm bone wet weight) | | | Acid phosphatase[a] Tartrate Insensitive (mU/gm bone wet weight) | | |
|---|---|---|---|---|---|---|
| | Control | Treated | p | Control | Treated | p |
| Femur | 155(±24) | 284 (±19) | <0.001 | 31(±5) | 60(±7) | <0.001 |
| Skull | 405(±44) | 1075 (±84) | <0.001 | 355(±42) | 607(±52) | <0.001 |
| Sternum | 46(±2) | 93 (±7) | <0.001 | 107(±16) | 137(±14) | NS |

[a]All data reported as mean ± S.E.M. and based on observations from at least 10 rats in each group.
[b]Comparisons of treated versus control were by the students' T test.
[c]Not significant at $p < 0.05$.

TABLE 5

In Vivo Effect Of Bovine Bone IGF-II Extract On the Tibiae Of Rats (Experiment 2)

| | Parameter | Control | Treated[a] | p[b] |
|---|---|---|---|---|
| 1. | Tibiae Periosteal Bone Formation (mm$^2$) | 0.45(±0.02) | 0.72(±0.04) | <0.001 |
| 2. | Tibiae Periosteal Bone Apposition Rate ($\mu$/day) | 8.58(±0.33) | 12.07(±0.51) | <0.001 |

[a]All data reported at mean ± S.E.M. and based on observations from at least 10 rats in each group.
[b]Comparisons of treated versus control were by the students' T test.

A second more detailed experiment on the in vivo effects of parenteral administration of bovine bone IGF-II extract similarly indicates that IGF-II significantly increases osteoblastic activity within the bone (Tables 3–5).

In this second experiment, Experiment 2, ten rats were used in both the Treated and Control groups. As in Experiment 1, the serum calcium and body weight remained unchanged with treatment (Table 3).

In Experiment 2, the levels of bone alkaline phosphatase were analyzed more extensively. Again, the Treated group exhibited significantly increased levels of alkaline phosphatase in the femur, skull and sternum over that exhibited by the Control group, 83%, 165%, and 102% respectively—parameters 1, 2, and 3 of Table 4. The acid phosphatase levels, although increased, were only significantly increased (p<0.001) in the femur and skull of the Treated group and by 93%, and 71% respectively.

The results of the alkaline phosphatase analysis in the femur, skull and sternum are consistent with an increase in osteoblast number and bone formation. The alkaline phosphatase data also agrees very well with the quantitative histology of the tibiae of treated rats, where a 60% increase (p<0.001) in the periosteal bone formation (mm$^3$) and a 40% increase in the matrix apposition rate ($\mu$/day) were observed. (Table 5).

As in Experiment 1, the increase in tartrate sensitive acid phosphatase in the femur and skull is consistent with an increase in the amount of osteoblastic acid phosphatase due to the increased number of osteoblasts. It is also consistent with the presence of the osteoclast stimulating agent, beta transforming growth factor (TGF) in the bone extract.

To obtain pure human IGF-II, human bone cells are preferably grown in monolayer culture in dishes containing Dulbecco's modified Eagle's medium supplemented with 10% fetal calf serum. The release of the polypeptide IGF-II, into the culture medium increases with increasing culture time.

The production of IGF-II is modulated by systemic agents. In the human bone cell monolayer culture model described above, the addition of insulin (10–10,000 ng/ml) for twenty four hours stimulates the production of IGF-II by the bone cells in a dose dependent manner (Table 6).

TABLE 6

Effect of insulin on the secretion of IGF-II by human bone cells in vitro.

| Insulin added (ng/ml) | IGF-II levels (ng/ml) after insulin exposure during | |
|---|---|---|
| | 0–24 hours | 24–48 hours |
| 0 | 17.2 ± 5.0 | 12.5 ± 5.0 |
| 10 | 16.7 ± 1.0 | 12.0 ± 5.0 |
| 100 | 22.6 ± 8.5 | 16.0 ± 9.0 |
| 1000 | 24.6 ± 6.5 | 19.0 ± 11.5 |
| 10000 | 32.0 ± 7.0 | 28.0 ± 1.0 |

Treatment of human bone cells in culture with human growth hormone (10 ng/ml) for five days also increases IGF-II production by 50% (p less than 0.01). Additionally, human somatostatin (50 ng/ml) also stimulates IGF-II production by 148% of control by human bone cells in culture compared with untreated controls (p less than 0.01).

Human bone cells in culture produce much more IGF-II than IGF-I. For example, media conditioned by $2 \times 10^4$ cells for 24 hours contains 17.6 ng/ml of IGF-II. However, during the same period under identical culture conditions, the cells produced only 1.16 ng/ml of IGF-I. Thus, human bone cells are shown to produce greater than fifteen times (15x) more IGF-II than IGF-I.

The mitogenic activity of purified IGF-II on pre-osteoblasts is reflected in Table 7. Specifically, Table 7 indicates that IGF-II stimulates the proliferation of embryonic chick calvarial bone cells (pre-osteoblasts) in a monolayer culture. Moreover, the rate of proliferation increases with increasing GF-II concentration.

TABLE 7

Effects of IGF-II on bone cell proliferation in embryonic chick calvarial cells in monolayer culture.

| IGF-II Conc. (ng/ml) | $^3$H-Thymidine INCORPORATION (% of unstimulated control) |
|---|---|
| 0 | 100 ± 13 |
| 0.3 | 202 ± 32 |
| 1.0 | 269 ± 46 |
| 3.0 | 338 ± 39 |
| 10.0 | 403 ± 54 |
| 30.0 | 412 ± 20 |

Data are mean ± standard deviation of six replicates (basal counts = 351 ± 46, n = 6).

In a similar experiment conducted on human bone cells, purified human IGF-II at a concentration of 2 ng/ml stimulated the proliferation of human bone cells at 362% of the Control value (Table 8).

TABLE 8

Effect Of Human IGF-II On The Proliferation Of Human Bone Cells.

| Treatment | Concentration | CPM | % Of Control | Significance |
|---|---|---|---|---|
| Control | | 316 ± 81 | 100 | |
| human IGF-II[a] | 2 ug/ml | 1146 ± 80 | 362 ± 80 | p < .001 |
| serum | 1% | 2479 ± 816 | 897 ± 165 | p < .001 |

Data are expressed as mean + 1 SD of six samples, Significance expressed compared to control (Students t Test).
[a] = Partially purified human IGF-II This enhanced mitogenic activity in the chick and human bone cell cultures, which was stimulated by IGF-II, is directly translatable into enhanced osteoblastic (bone producing) activity within the bone. It is to be noted that when purified human IGF-II was added to cultures of embryonic mouse calvariae prelabelled with the isotope $^{45}$calcium, IGF-II had no significant effect on the release of the $^{45}$calcium from these bones, indicating a lack of any stimulatory effect on bone resorption.

Thus, by using IGF-II in therapeutically effective amount, it is possible to increase the osteoblastic activity within the bone to a point exceeding the pre-existing osteoclastic activity so as to effect a cure in a patient suffering from an osteopenia.

Similarly, IGF-II can be administered to a patient susceptible to an osteopenia in a prophylactically effective amount, so as to maintain a balance between osteoblastic and osteoclastic activity in said patient.

In a particularly preferred embodiment of the present invention, the osteopenia being treated or prevented is osteoporosis of all types.

While both IGF-II and fluoride ion increase the proliferation of human bone cells (Table 9) as determined by the incorporation of tritiated thymidine into DNA, the combination of IGF-II and fluoride ion produces an unexpectedly enhanced effect upon bone cell proliferation, said fluoride ion potentiating the osteoblastic stimulating activity of IGF-II (Table 10). In addition, fluoride is the single most effective agent for restoring bone mass lost as a result of osteoporosis, and, at levels that are effective in stimulating bone formation, fluoridet particularly as a slow release preparation does not have appreciable side effects on other organ systems.

TABLE 9

Effect Of IGF-II And Fluoride On Thymidine Incorporation Into DNA By Cultured Human Bone Cells And Human Skin Fibroblasts.

| CELL TYPE | BOVINE IGF-II (8.5 ug/ml) | | FLUORIDE (20 mM) | |
|---|---|---|---|---|
| | PERCENTAGE OF CONTROL | | | |
| Human bone | 370 ± 62 | p .01 | 252 ± 52 | p < .01 |
| Chick bone | 538 ± 71 | p .01 | 140 ± 38 | p < .05 |
| Human skin | 271 ± 84 | p .01 | 87 ± 3 | |

Data expressed as mean ± SD, Control incorporation rates in cpm were 430 ± 400 (Human bone), 315 ± 50 (chick bone), and 1019 ± 485 (human skin).

Accordingly, the combination of IGF-II and fluoride ion, wherein the fluoride ion (in a physiologically acceptable form such as MFP, NaF or other) is associated with a pharmaceutically acceptable cation, would provide an especially effective pharmaceutical agent in the treatment of the osteopenias, particularly osteoporosis.

Such pharmaceutically acceptable cations include sodium, potassium, lithium, calcium, magnesium, ferrous, zinc, copper, manganous, aluminum, ferric, manganic and the like. Particularly preferred are the ammonium, potassium, sodium, calcium and magnesium salts.

It is well known in the art that fragments of biologically active polypeptides, either alone or attached to other non-interferring peptides, polysaccharides, aldoses, and like molecules, can possess substantially the same biological activity as the parent intact polypeptide. Accordingly, this invention also encompasses fragments of IGF-II also possessing osteoblastic stimulating activity, whether obtained from an intact molecule or synthetically such as by chemical manipulation or by recombinant DNA techniques.

It is also within the scope of this invention to employ said osteoblastic stimulating fragments alone or in combination with fluoride ion to treat or prevent the osteopenias, particularly osteoporosis, in patients suffering from or susceptible respectively to said disease states.

TABLE 10

Interaction between fluoride and bone extract containing chicken IGF-II on proliferation of calvarial bone cells.

| | Effector | $^3$H-thymidine incorporation | Signif. Diff. from controls. |
|---|---|---|---|
| a) | Control | 100% +/− 13% | — |
| b) | Con + bone extract | 185% +/− 17% | p < .001 |
| c) | Con + NaF | 175% +/− 21% | p < .001 |
| d) | Con + NaF + bone extract | 285% +/− 31% | p < .001 |

Legend: $^3$H-thymidine incorporation in chick calvarial cells in monolayer cultures, with incorporation shown as percent of untreated controls. Mean +/− S.D. in replicate calvarial cell cultures (n = 6). NaF = sodium fluoride used throughout at 100 uM. Bone extract was of embryonic chick bones and was used at 1 ug/ml throughout. $^3$H-thymidine incorporation in untreated cultures (controls) averaged 344 +/− 45 cpm/ culture well. When compared with a, b or c, d is significantly different at p < .001. The active factor in the chick bone extract is IGF-II (publication pending, J.R. Farley 1987).

Although IGF-II is only partially specific for bone cells, fluoride is much more specific for bone cells. Therefore, because fluoride potentiates the action of IGF-II and because fluoride is relatively bone specific, the combination therapy of fluoride and IGF-II enhances the bone response and not that of other tissues. Thus, fluoride targets the effects of IGF-II specifically to bone.

A veterinarian or physician of ordinary skill can readily determine whether a subject exhibits a bone wasting condition, osteopenia The compounds of this invention may be administered parenterally (other than by mouth) such as intravascularly, intraperitoneally, subcutaneously, intramuscularly, or by suppository using forms known to the pharmaceutical art or by transdermal route (air gun or skin patch delivery). In the case of fractures, the compounds may, in addition to the above methods, be administered locally, into, at or near the fracture site.

For intravascular, intraperitoneal, subcutaneous, or intermuscular administration, the active drug components of the present invention in liquid, powdered, or lyophilized form may be combined with a suitable diluent or carrier (collectively referred to herein as "carrier" materials) such as water, saline, aqueous dextrose, aqueous buffers, and the like. Preservatives may also be added.

Regardless of the route of administration selected, the compounds of the present invention are formulated into pharmaceutically acceptable dosage forms by conventional methods known to those skilled in the art. The compounds may also be formulated using pharmacologically acceptable acid or base addition salts. Moreover, the compounds or their salts may be used in a suitable hydrated form.

Regardless of the route of administration selected, a non-toxic but therapeutically effective quantity of one or more compounds of this invention is employed in any treatment. The dosage regimen for preventing or treating a bone wasting condition with the compounds of this invention is selected in accordance with a variety of factors, including the type, age, weight, sex, and medical condition of the patient, the severity of the inflammatory condition, the route of administration, and the particular compound employed in the treatment. A physician or veterinarian of ordinary skill can readily determine and prescribe the effective amount of the drug required to prevent or arrest the progress of the condition. In so proceeding, the physician or veterinarian could employ relatively low doses at first and subsequently increase the dose until a maximum response is obtained.

IGF-II can be prepared from bone or bone cells or various species by at least three methods. The first is by extraction from bone extract. The second by production by bone cells in culture. The third (and what may ultimately be the preferred) method of preparation of pure IGF-II involves recombinant DNA techniques. The first stage in such techniques (i.e., recombinant DNA) would be to obtain a length of DNA coding for the desired IGF-II. One way to do this would be to isolate mRNA from IGF-II producing cells and, with the in vitro use of reverse transcriptase, produce cDNA coding for the desired peptide. Alternatively, the DNA may be chemically synthesised. A number of oligonucleotides may be produced, from which the desired cDNA can be prepared by the use of DNA ploymerase and DNA ligase. Restriction endonuclease digestion of either end can leave appropriate cohesive restriction sites for insertion into a plasmid.

Whether the synthetic DNA is cDNA or chemically synthesised, it can either have cohesive ends provided by a restriction endonuclease or it may be terminally tailed by, for example, oligo-dC, by the use of the appropriate nucleotide and terminal transferase, Whichever tailing method is chosen, a plasmid (for example pBR322) can then be taken and cleaved at a single site by a restriction endonuclease such as PstI. Digested pBR322 can be oligo-dG tailed to complement an oligo-dC tail piece of DNA coding for the desired peptide. The cleaved plasmid and the DNA coding for the peptide can be annealed and ligated; host cells (for example *E. coli*) can be transformed with the appropriate recombinant plasmid.

The transformed *E. coli* host cells may be cultured under appropriate conditions to express the IGF-II peptide.

It should be noted that it is not envisaged that production by recombinant DNA techniques should be limited to bacterial systems. Eukaryotic systems such as yeast systems can also be used and may in practice be preferred.

The following examples give specific details regarding the production of IGF-II from bone or bone cells of various species.

EXAMPLE 1

Preparation of a Highly Purified Human Insulin-like Growth Factor-II (hIGF-II) from Extract.

Extraction of human IGF-II.

Human femoral heads obtained during hip replacement surgery were cleaned with a knife to remove the adhering soft tissue. The bones were then cut into small pieces (approx. 2 cm$^3$) using a band saw and washed with cold tap water to remove the blood and marrow. The bone pieces were frozen in liquid nitrogen and ground with solid $CO_2$ using a Wiley mill. The resulting bone powder (2 mm$^3$) was washed overnight by constant mixing with deionized water containing proteinase inhibitors (5 mM benzamidine, 100 mM $\epsilon$-aminocaproic acid and 1 mM phenylmethylsulfonyl fluoride). After washing with deionized water, the residue was extracted for 72–96 h by constant stirring with excess (5 vol.) 30 mM Tris-acetate/4M guanridine-HCl (pH 7.4) containing proteinase inhibitors. By this extraction, serum proteins (albumin, immunoglobulins, etc.) and other loosely bound proteins were extracted. The supernatant was decanted (guanidine extract I) and the residue was re-extracted for an additional 24 h with 4M guanidine solution (guanidine extract II). After the guanidine extraction, the residue was demineralized for 7 days by constant mixing with 10% EDTA/4M guanidine-HCl containing proteinase inhibitors (pH 7.4). The supernatant was decanted, centrifuges (10,000 rpm for 20 min.), filtered and concentrated by Amicon membrane filtration. The concentrate (guanidine-EDTA extract) was washed with excess of 4M guanidine-HCl to remove EDTA completely. The guanidine-EDTA extract was used for further human IGF-II purification under dissociative conditions. For EDTA extraction, the bone powder was extracted with 10% EDTA (without guanidine extraction) as described previously (3). Aliquots of guanidine extract, guanidine-EDTA extract and EDTA extract were dialyzed against distilled water using Spectrapor membrane tubing (molecular weight cut-off, 3500), assayed for protein concentration, and tested for mitogenic activity.

Purification of Human IGF-II.

Hydroxyagatite chromatography. Hydroxyapatite (Fast Flow, Bio-Rad) was equilibrated with 30 mM Tris-acetate/4M guanidine-HCl/10 mM potassium phosphate (pH 7.4). The phosphate concentration of the guanidine-EDTA extract was adjusted to 10 mM and the sample was applied to the hydroxyapatite column (15×5 cm). The unbound proteins were eluted with 10 mM phosphate in 30 mM tris-acetate/4M guanidine-HCl (pH 7.4). The bound proteins were eluted in a single step by increasing the phosphate concentration to 400 mM in the same buffer. Aliquots of unbound and 400 mM phosphate-eluted fractions were desalted by dialysis and tested for protein concentration and mitogenic activity.

HPLC gel-filtration chromatography. The unbound fraction from hydroxyapatite chromatography (which contained 90% of the mitogenic activity) was concentrated and the proteins were separated by HPLC gel-filtration chromatography on a preparative TSK-G3000 SWG column (21.5×600 mm, LKB Products). The chromatography was performed with a Beckman model 344 gradient liquid chromatography system, which consists of two Model 112 pumps controlled by a Model 421 controller-programmer. 2 ml samples were applied to the column with an Altex Model 210 injection valve and the proteins were eluted at 2 ml/min with 30 mM Tris-acetate/4M guanidine-HCl (pH 7.4). The absorbence was monitored at 280 nm (Beckman model 160 detector) and the elution profile was recorded using a Hewlett Packard Integrator Model 3390A integrating recorder. 2-min fractions were collected and the fractions were pooled according to the protein peaks and concentrated. Aliquots of the pools were dialyzed against distilled water to remove guanidine and assayed for protein content and mitogenic activity.

Affinity Chromatography.

The active pool obtained from gel filtration (6 to 17.5 kDa) was dialyzed against 10 mM Tris-HCl, (pH 7.2) containing 100 mM NaCl and was loaded in 10 ml of the same buffer onto a 0.5×10 cm heparin-sepharose affinity column (Pharmacia FPLC system). The unbound proteins were eluted with the starting buffer (20 minutes, flow rate 1 ml/min, 2 minute fractions) and the bound proteins were eluted by a gradient of 0.1 to 3.0M NaCl over 100 minutes. Fractions were diluted in 1 mg bovine serum albumin per ml Dulbecco's modified Eagle's medium (DMEM) and tested for biological activity using ($^3$H) Thymidine incorporation into the DNA of chick embryo bone cells in serum-free monolayer culture. The active fractions from heparin sepharose chromatography (Fractions 15–30, 0.3 to 0.6M NaCl) were pooled and rerun on the same heparin-sepharose column using the same gradient. The active fractions from the second heparin sepharose step (Fractions 17–22) were pooled, concentrated and then subjected to 2 sequential separations by reverse phase chromatography in 0.1% trifluoroacetic acid (TFA) using a 4.6×250 mm C-4 column (Bio-Rad RP 304). The first separation used a 10–60% acetonitrile gradient in 50 minutes and the second separation used a 25–45% acetonitrile gradient in 100 minutes. Final purification of human IGF-II was achieved by HPLC reverse phase chromatography in 0.1% TFA using a 3.9×150 mm microbondapak CN column (Waters Corporation) with a 1-propanol gradient (20–40% in 100 minutes). HPLC reverse phase chromatography was done using a Beckman model 344 gradient liquid chromatography system with a 214 nm detector. Fractions were concentrated by evaporation under reduced pressure.

The protein in the different fractions were dissolved either in physiological saline (0.9% NaCl) for use in vivo, or in distilled water for determinations of mitogenic activity in monolayer bone cell culture.

EXAMPLE 2

Preparation of Bovine Insulin-like Growth Factor II (bIGF-II) from Extract

The thigh bones from freshly slaughtered cows are mechanically scraped clean of soft tissue and cut into 2 cm³ sections. The bone sections are frozen in liquid nitrogen and ground in a Wiley mill to yield a bone powder that is washed with warm water to remove fat and serum protein, demineralized and extracted using 20% EDTA, 0.04% sodium azide as described above. The EDTA extracts are concentrated and partially desalted by Amicon ultrafiltration. The remaining EDTA is removed by desalting with Sephadex G-25. Three alternative methods can be used for further purification of the desalted crude extracts.

1. Gel filtration on Agarose yields an active bIGF-II fraction having a MW range of 150 to 200 kdal, probably consisting of bIGF-II bound to its binding protein or pre-IGF-II.

2. Direct purification of the crude extract on DEAE Sephacel yields a large bIGF-II fraction that is modestly bound. In addition, active bIGF-II fractions that are unbound or weakly bound to DEAE Sephacel are obtained in the range of 10 to 20 kdal.

3. Purification of desalted crude extract on hydroxyapatite yields a non-active fraction that elutes with 0.15M phosphate in an active fractions that is recovered by dissolving the hydroxyapatite support with EDTA. The tightly bound fraction yields approximately equal amounts of large BIGF-II and small bIGF-II.

The large partially purified bIGF-II tends to become small on further manipulation. Evidence suggests that an endogenous bone protease is present in the bone extracts and is activated during the purification process. This protease is evident in the bovine bone extracts as will be indicated subsequently in chicken extracts, but is not observed in the purification of the human extracts.

EXAMPLE 3

Preparation of Chicken Insulin-like Growth Factor (II) (cIGF-II) from Extract

The tibia and femur of adult chickens are mechanically scraped clean of soft tissue. The cartilage ends are cut off and the bones are frozen in dry ice and smashed into 3 mm³ pieces. Serum proteins and fat are removed by extensive washing of the bone pieces in 0.03M Tris(acetate), 0.15M NaCl, (pH 7.4), with vigorous agitation. The bone is then subjected to demineralization and extraction with 10% EDTA, 0.04% sodium azide. The EDTA extracts are concentrated and partially desalted by Amicon ultrafiltration and the remaining EDTA removed by Sephadex G-25 chromatography. Two approaches are used to further purify the cIGF-II.

1. Gel filtration of the desalted crude extract on Agarose 0.05M yields predominately a large form of cIGF-II (100 to 200 kdal), as well as small quantities of the small cIGF-II in the 10 to 20 kdal range.

2. DE-52 chromatography of the desalted crude bone extract yields a cIGF-II fraction that is weakly bound to the matrix. The weakly bound fraction behaves like large cIGF-II when chromatographed on a TSK 3000 HPLC gel filtration column shortly after isolation. Preincubation of the weakly bound fraction before HPLC gel filtration results in a shift of large cIGF-II to the smaller cIGF-II. This change in apparent size is believed to be a result of the presence of a protease which is detected in the fraction weakly bound to DE-52. The cIGF-II activity in the desalted crude extracts binds to hydroxyapatite, QAE cellulose and DE-52, but does not bind to collagen linked to Agarose or to carboxymethyl Sepharose.

EXAMPLE 4

Production of Human Insulin-like Growth Factor-II by Human Bone Cells in Culture Human bone cells were collagenase dissociated and grown in monolayer culture in 24 well dishes containing Dulbecco's modified Eagle's medium (DMEM) supplemented with 10% fetal bovine serum (FBS). HIGF-II is released into the culture medium by the bone cells as they grow.

As noted in the detailed discussion (Table 6), insulin can be added in varying amounts to increase the amount of hIGF-II produced. Similarly, human growth hormone (10 ng/ml) or somatostatin (50 ng/hl) can also be used to enhance hIGF-II production (see detailed discussion).

Extraction and purification are performed as in Example 1.

What is claimed is:

1. A method of treating osteoporosis in a human comprising administering thereto a therapeutically effective amount of a pharmaceutical agent having the amino acid sequence:

Ala—Tyr—Arg—Pro—Ser—Glu—Thr—Leu—Gly—Gly—
10

Gly—Glu—Leu—Val—Asp—Thr—Leu—Gln—Phe—Val
20

Cys—Gly—Asp—Arg—Gly—Phe—Tyr—Phe—Ser—Arg—
30

Pro—Ala—Ser—Arg—Val—Ser—Arg—Arg—Ser—Arg
40

Gly—Ile—Val—Glu—Glu—Cys—Cys—Phe—Arg—Ser—
50

Cys—Asp—Leu—Ala—Leu—Leu—Glu—Thr—Tyr—Cys
60

Ala—Thr—Pro—Ala—Lys—Ser—Glu.

* * * * *